US007201895B2

(12) United States Patent
Gordon et al.

(10) Patent No.: US 7,201,895 B2
(45) Date of Patent: Apr. 10, 2007

(54) HIGH-AFFINITY ANTAGONISTS OF ELR-CXC CHEMOKINES

(75) Inventors: John R. Gordon, Saskatoon (CA); Fang Li, Dalian (CN)

(73) Assignee: University of Saskatchewan Technologies Inc., Saskatoon, Saskatchewan (CA)

( * ) Notice: Subject to any disclaimer, the term of this patent is extended or adjusted under 35 U.S.C. 154(b) by 461 days.

(21) Appl. No.: 10/087,273

(22) Filed: Mar. 1, 2002

(65) Prior Publication Data

US 2003/0077705 A1 Apr. 24, 2003

Related U.S. Application Data

(60) Provisional application No. 60/273,181, filed on Mar. 1, 2001.

(51) Int. Cl.
*A61K 38/19* (2006.01)
*C07K 14/52* (2006.01)

(52) U.S. Cl. ..................................... 424/85.1; 530/324

(58) Field of Classification Search ................ 530/324; 424/85.1, 85.2
See application file for complete search history.

(56) References Cited

FOREIGN PATENT DOCUMENTS

| | | | |
|---|---|---|---|
| WO | WO 97/00601 | * | 1/1997 |
| WO | PCT/CA02/00271 | | 1/2002 |

* cited by examiner

*Primary Examiner*—Prema Mertz
(74) *Attorney, Agent, or Firm*—Michael R. Williams; Adrian D. Battison; Ryan W. Dupis

(57) ABSTRACT

The present invention provides novel nucleic acids, novel polypeptide sequences encoded by these nucleic acids, methods for production thereof, and uses thereof, for a novel ELR-CXC chemokine receptor antagonist.

6 Claims, 7 Drawing Sheets

HIGH-AFFINITY ANTAGONISTS OF ELR-CXC CHEMOKINES

CROSS REFERENCE TO RELATED APPLICATION

This application claims the benefit of U.S. Provisional Patent Application No. 60/273,181, filed on Mar. 1, 2001.

FIELD OF THE INVENTION

The present invention relates to the field of CXC chemokine receptor antagonists.

BACKGROUND OF THE INVENTION

The CXC chemokines that possess the receptor-signaling glutamic acid-leucine-arginine (ELR) motif (e.g., CXCL1/GROα, CXCL8/IL-8; ref. 1) are important to the influx of inflammatory cells that mediates much of the pathology in multiple settings, including ischemia-reperfusion injury (ref. 2, 3), endotoxemia-induced acute respiratory distress syndrome (ARDS; ref. 4), arthritis, and immune complex-type glomerulonephritis (ref. 5). For instance, inappropriately released hydrolytic enzymes and reactive oxygen species from activated neutrophils initiate and/or perpetuate the pathologic processes. On the other hand, during most bacterial infections this chemokine response represents a critical first line of defense, but even here $ELR^+$ CXC chemokine responses can, via their abilities to activate inflammatory cells displaying the CXCR1 and CXCR2 receptors, exacerbate the pathology. For example, during experimental 'cecal puncture and ligation' sepsis, neutralization of MIP-2 reduces mouse mortality from 85 to 38% (ref. 6). Infect. Immun. 65:3847–3851). And experimental treatments that eliminate circulating neutrophils ameliorate the pathology of pneumonic mannheimiosis (ref. 7), wherein CXCL8 expression in the airways variably effects the neutrophil chemoattraction (ref. 8, 9). Despite the critical importance of these chemokine responses in many settings, wayward inflammatory cell responses are sufficiently damaging that the development of therapeutic tools with which we can block $ELR^+$ chemokines has become a research priority (ref. 10).

The 'ELR' chemokines chemoattract and activate inflammatory cells via their CXCR1 and CXCR2 receptors (ref. 1, 11). The CXCR1 is specific for CXCL8 and CXCL6/granulocyte chemotactic protein-2 (GCP-2), while the CXCR2 binds CXCL8 with high affinity, but also macrophage inflammatory protein-2 (MIP-2), CXCL1, CXCL5/ENA-78, and CXCL6 with somewhat lower affinities (see, for example, ref. 10). CXCL8 signaling in cell lines transfected with the human CXCR1 or CXCR2 induces equipotent chemotactic responses (ref. 13, 14), and while neutrophil cytosolic free $Ca^{++}$ changes and cellular degranulation in response to CXCL8 are also mediated by both receptors, the respiratory burst and activation of phospholipase D reportedly depend exclusively on the CXCR1 (ref.16). On the other hand, it has been reported that a non-peptide antagonist of the CXCR2, but not the CXCR1, antagonizes CXCL8-mediated neutrophil chemotaxis, but not cellular activation (ref. 17). Finally, there is abundant evidence that chemokines are most often redundantly expressed during inflammatory responses (see, for example, ref. 8). But, despite active research in the field, no CXC chemokine antagonists are known in the prior art that are effective in suppressing adverse inflammatory cell activity induced by either ELR-CXC chemokine receptor.

SUMMARY OF THE INVENTION

Compositions of the present invention include novel ELR-CXC chemokine antagonist proteins that are capable of binding to CXCR1 or CXCR2 receptors in mammalian inflammatory cells. These include antagonists that are capable of high-affinity binding, wherein "high-affinity" refers to the antagonist's affinity for the receptor being at least about one order of magnitude greater than that of the wild-type chemokine agonist. The novel antagonist proteins also include those that are substantially equivalent (that is, those that contain amino acid substitutions, additions and deletions that do not delete the CXCR1 and CXCR2 binding functions) to a wild-type bovine CXCL8 protein (illustrated herein as the amino acid sequence of SEQ ID NO:2) and also bear a truncation of the first two amino acid residues along with substitutions of Lys11 with Arg and Gly31 with Pro. Analogues of this $CXCL_{(3-74)}$K11R/G31P are also included, namely $CXCL_{(3-74)}$K11R/G31P/P32G and $CXCL_{(3-74)}$K11R/T12S/H13F/G31P. In addition, compounds having a three dimensional structure resulting in high affinity binding to CXCR1 or CXCR2 receptors in mammalian inflammatory cells.

Other compositions of the invention are novel polynucleotides and polypeptides relating to these proteins. One such novel polynucleotide is the nucleotide sequence identified herein as SEQ ID NO:4, while one such novel polypeptide is the amino acid sequence identified herein as SEQ ID NO:1. Further, the invention includes vectors comprising the novel polynucleotides, and expression vectors comprising the novel polynucleotides operatively associated with regulatory sequences controlling expression of the polynucleotides. Similarly, gene fusions comprising affinity handles and the novel polynucleotides are included in the invention, as are the resultant vectors and expression vectors containing such gene fusions.

The invention also includes hosts genetically engineered to contain the novel polynucleotides as well as hosts genetically engineered to contain the novel polynucleotides operatively associated with regulatory sequences, that is, associated with regulatory sequences in such a fashion that the regulatory sequences control expression of the novel polynucleotides. Also included are hosts containing gene fusions, either associated with regulatory sequences in such a fashion that the regulatory sequences control the expression of the gene fusions, or in the absence of such regulatory sequences. These hosts may be viruses or cells, wherein the latter include without limitation bacteria, yeast, protozoa, fungi, algae, plant cells, and animal cells and higher organisms derived therefrom.

The invention additionally comprises uses of the novel polypeptides in treating CXC chemokine-mediated pathologies involving the CXCR1 or CXCR2 receptors in mammals. Likewise, the invention includes methods of treating ELR-CXC chemokine-mediated pathologies involving the CXCR1 or CXCR2 receptors, comprising administering to the afflicted mammal an effective amount of one of the novel polypeptides. Pharmaceutical compositions comprising a biologically-active amount of one of the novel polypeptides are also included in the invention.

Finally, methods of producing and purifying the novel polypeptides are also included in the invention.

Figure 1:
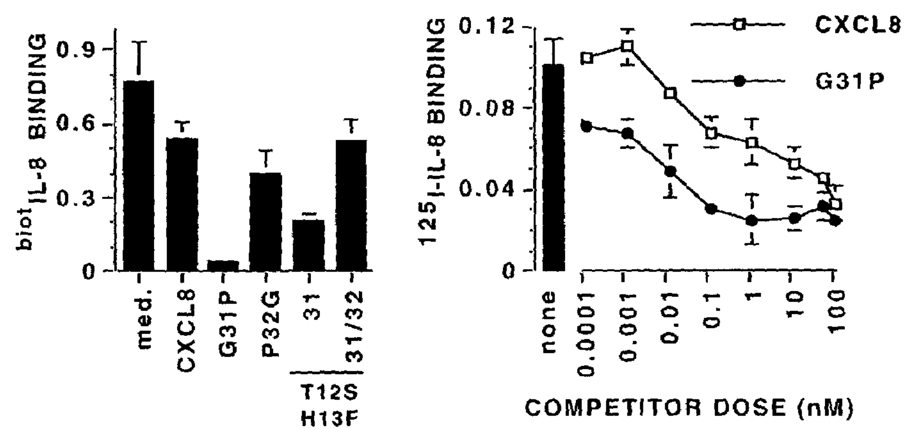
FIG. 1. The G31 P analogue of $CXCL8_{(3-74)}$K11R is a potent inhibitor of CXCL8-binding to peripheral blood neutrophils. Bovine peripheral blood neutrophils (87–93% purity) were (upper panel) exposed at 4° C. for 2 h to $CXCL8_{(3-74)}$K11R analogues (10 ng/ml) or medium (med) alone, then washed and similarly incubated with biotinylated CXCL8 ($^{biot}$CXCL8; 1000 ng/ml or 129 nM). These levels of CXCL8 approximate those found in the lung tissues of animals with pneumonic pasteurellosis (ref. 8, 9). The levels of $^{biot}$CXCL8 binding to the cells were determined using ELISA technology. The depicted amino acid substitutions within $CXCL8_{(3-74)}$K11R included: G31P; P32G; T12S/H13P/G31P; and T12S/H13P/G31P/P32G. The G31P, but not the P32G, analogue was a highly effective antagonist of CXCL8 binding to the cells. With both the G31P and P32G analogues, additional substitutions of T12S and H13F reduced their CXCL8 antagonist activities (lower panel). Neutrophils were exposed simultaneously for 45 min at 4° C. to varying concentrations of $CXCL8_{(3-74)}$K11R/G31P or unlabeled CXCL8 and 20 pM $^{125}$I-CXCL8. This level of $^{125}$I-CXCL8 was chosen as nearly saturating for the cell's high affinity CXCL8 receptors (data not shown). The levels of cell-associated $^{125}$I-CXCL8 were assessed using a counter. The data clearly indicate that $CXCL8_{(3-74)}$K11R/G31P had a substantially higher affinity for the neutrophils than CXCL8.

DETAILED DESCRIPTION OF THE INVENTION (The following abbreviations are used throughout this disclosure: ARDS, acute respiratory distress syndrome; BALF, bronchoalveolar lavage fluid(s); BHR, Bolton-Hunter Reagent; CXCR1, CXCR2, CXCL8 receptors A, B, respectively; ELR, glutamic acid-lysine-arginine motif; CXCL1, growth-related oncogenealpha; CXCL4, platelet factor-4; CXCL5, epithelial-derived neutrophil activator-78; CXCL6, granulocyte chemotactic protein-2; CXCL8, interleukin-8; fMLP, formyl methionyl-leucylproline bacterial tripeptide; IPTG, isopropyl-thio-D-galactopyranoside; MIP-2, macrophage inflammatory protein-2; PMSF, phenylmethylsulfonyl fluoride; TMB, tetramethylbenzidine.)

When amino terminal truncation of bovine CXCL8 is combined with a lysine to arginine substitution at amino acid 11 (i.e., $CXCL8_{(3-74)}$K11R), dramatic increases in CXCR1 and CXCR2 receptor affinity are evident, such that $CXCL8_{(3-74)}$K11R competitively inhibits the binding of multiple ligands to both receptors (ref. 24). Further truncation into the receptor-signaling ELR motif (e.g., amino acids 4–6 of human CXCL8) of some CXC chemokines can transform them into mild ($CXCL8_{(6-72)}$) to moderate ($CXCL1_{(8-73)}$) receptor antagonists (ref. 15, 25). As disclosed herein, the introduction into bovine $CXCL8_{(3-74)}$ K11R of a second amino acid substitution, glycine 31 to a proline residue (i.e., $CXCL8_{(3-74)}$K11R/G31P), renders this CXCL8 analogue a very high affinity antagonist of bovine and human ELR-CXC chemokine responses. It fully antagonizes the entire array of ELR-CXC chemokines expressed within bacterial or endotoxin-induced inflammatory foci and blocks endotoxin-induced inflammation in vivo.

Although the following discussion deals primarily with bovine neutrophils, other mammalian (including human) inflammatory cells also display CXCR1 and CXCR2 receptors (see, for example, ref. 52) and so are vulnerable to inhibition by $CXCL8_{(3-74)}$K11R/G31P. Accordingly, the present invention has broad applicability to mammalian ELR-CXC chemokine-mediated pathologies.

In an alternate embodiment of the invention, it is envisioned that compounds having the same three dimensional structure at the binding site may be used as antagonists. Three dimensional analysis of chemical structure is used to determine the structure of active sites, including binding sites for chemokines. Chemical leads with high throughput screening have been used to generate and chemically optimize a selective antagonist of the CXCR2 (ref. 17). A similar approach was also used to generate a CCR3 antagonist (ref. 56).

Wells et al (ref. 57), has employed nuclear magnetic resonance spectroscopy (NMR) to detail the three dimensional structure of ligands for CXCR, including both ELR and non-ELR CXC chemokines. With their NMR information, Wells et al generated multiple substitutions within the receptor binding sites of multiple chemokines, such that they could substantially alter the ligands' receptor specificities.

Material and Methods

Reagents & supplies. The following reagents were purchased commercially: glutathione-Sepharose, the expression vector pGEX-2T, Sephadex G-25 (Amersham-Pharmacia-Biotech, Baie d'Urfé, PQ), Bolton-Hunter reagent, a protein biotinylation kit (Pierce Scientific, Rockford, Ill.), the sequencing vector pBluescript II KS, Pfu Turbo™ DNA polymerase (Stratagene, La Jolla, Calif.), a site-directed mutagenesis kit (QuickChange™; Boerhinger-Mannheim Canada, Laval, PQ), aprotinin, benzene, calcium ionophore A23187, chloramine T, cytochalasin B, dimethylformamide, endotoxin (*Escherichia coli* lipopolysaccharide, serotype 0127B8), isopropyl-thio-D-galactopyranoside (IPTG), leupeptin, p-nitrophenyl-β-D-glucuronide, mineral oil, silicon oil, tetramethylbenzidine (TMB), phenylmethylsulfonyl fluoride (PMSF), phorbol-12,13-myristate acetate (PMA), and Triton X-100 (Sigma Chemical Co, Mississauga, ON), a Diff-Quick staining kit (American Scientific Products, McGaw Pk, Ill.), human CXCL1, CXCL5, and CXCL8 (R & D Systems Inc, Minneapolis, Minn.), horse radish peroxidase (HRP)-conjugated anti-rabbit Ig (Zymed, South San Francisco, Calif.), DMEM, HBSS (Gibco, Grand Island, N.Y.), HRP-streptavidin (Vector Labs, Burlingame, Calif.), ABTS enzyme substrate (Kirkegaard & Perry Labs, Gaithersburg, Md.), bovine serum albumin (BSA), and Lymphocyte Separation Medium (ICN Pharmaceuticals, Aurora, Ill.).

Generation of CXCL8.sub.$_{(3-74)}$K11R analogues. The high affinity CXCR1/CXCR2 ligand CXCL8.sub.$_{(3-74)}$ K11R, and its T12S/H13F analogue were generated in accordance with the methods described in Li and Gordon (ref. 24). The Gly31Pro (G31P), Pro32Gly (P32G), and G31P/P32G analogues of these proteins were similarly generated by site-directed mutagenesis using PCR with the appropriate forward and reverse oligonucleotide primers (Table 1). The products from each reaction were digested with DpnI, ligated into the vector pGEX-2T, transfected into HB101 cells, and their sequences verified commercially (Plant Biotechnology Institute, Saskatoon). Briefly, the recombinant bacteria were lysed in the presence of a protease inhibitor cocktail (2 mM PMSF, 2 μg/ml aprotinin, and 2 μg/ml leupeptin) and the recombinant fusion proteins in the supernatants purified by affinity chromatography, using glutathione-Sepharose beads in accordance with the methods of Caswell et al. (ref. 26). The $CXCL8_{(3-74)}$K11R analogues were cleaved from the GST fusion proteins by thrombin digestion, dialysed against phosphate buffered saline (PBS), run through commercial endotoxin-removal columns, and then characterized by polyacrylamide gel electrophoresis (PAGE) and Western blotting with a goat anti-bovine CXCL8 antibody (provided by Dr. M. Morsey). Each purified analogue had a molecular mass of 8 kDa, was specifically recognized by the anti-CXCL8 antibody in the Western blotting, and had a relative purity of 96%, as determined by densitometric analysis of the PAGE gels.

Labeling of the recombinant proteins. We used $^{biot}$CXCL8 for the initial surveys of analogue binding to neutrophils and $^{125}$I-CXCL8 for the later stage assays of relative receptor affinity. CXCL8 was biotinylated and the levels of biotin substitution determined using a commercial kit, as noted in Li and Gordon (ref. 24). The $^{biot}$CXCL8 was substituted with 2.15 moles of biotin per mole of CXCL8. CXCL8 was radiolabeled with $^{125}$I using the Bolton-Hunter Reagent (BHR) method, as noted in detail (ref. 24). The labeled protein was separated from the unincorporated $^{125}$I-BHR by chromatography on Sephadex G50, and the labeled CXCL8 characterized for its relative affinity for neutrophils and the time required to achieve binding equilibrium, as noted in Li and Gordon (ref. 24).

$CXCL8_{(3-74)}$K11R analogue binding assays. Cells (85–93% neutrophils) were purified from the blood of cattle in accordance with the Caswell method (ref. 26). In preliminary experiments, we determined that none of our analogues affected the viability of neutrophils, as determined by trypan blue dye exclusion. For the broad analogue surveys, neutrophils in HBSS/0.5% BSA were incubated for 2 h at 4° C. with the analogue, washed in cold DMEM, and then incubated for another 2 h at 4° C. with $^{biot}$CXCL8 (1000 ng/ml). The cell-associated biotin was detected by incubating the washed cells with alkaline phosphatase-conjugated streptavidin (1:700 dilution) and then with ABTS enzyme substrate. The $OD_{405}$ of the samples was determined using an ELISA plate reader. Medium-treated neutrophils routinely bound sufficient .sup.biotCXCL8 to generate an $OD_{405}$ of 0.5–0.6.

For the in-depth studies with $CXCL8_{(3-74)}$K11R/G31P, we used $^{125}$I-CXCL8 in binding inhibition assays with unlabeled CXCL8 or $CXCL8_{(3-74)}$K11R/G31P. In preliminary experiments we determined that the binding equilibrium time of neutrophils for $^{125}$I-CXCL8 was 45 min and that 20 pM $^{125}$I-CXCL8 just saturated the cell's high affinity receptors. Thus, in our assays, $10^6$ purified neutrophils were incubated for 45 min on ice with 20 pM $^{125}$I-CXCL8 and varying concentrations of unlabeled competitor ligand. The cells were then sedimented through 6% mineral oil in silicon oil and the levels of cell-associated radio-ligand determined using a counter. The non-specific binding of $^{125}$ICXCL8 to the cells was assessed in each assay by including a 200-fold molar excess of unlabeled ligand in a set of samples. This value was used to calculate the percent specific binding (ref. 27).

Neutrophil β-glucuronidase release assay. The neutrophil β-glucuronidase assay has been reported in detail (ref. 24). Briefly, cytochalasin B-treated neutrophils were incubated for 30 min with the CXCL8 analogues, then their secretion products assayed colorimetrically for the enzyme. β-Glucuronidase release was expressed as the percent of the total cellular content, determined by lysing medium-treated cells with 0.2% (v/v) Triton X- 100. Neutrophil challenge with the positive control stimulus PMA (50 ng/ml) and A23187 (1 μg/ml) induced 42+/−6% release of the total cellular β-glucuronidase stores.

Samples from inflammatory lesions. We obtained bronchoalveolar lavage fluids (BALF) from the lungs of cattle (n=4) with diagnosed clinical fibrinopurulent pneumonic mannheimiosis (ref. 8), as well as teat cistern wash fluids from cattle (n=4) with experimental endotoxin-induced mastitis (ref. 28). In preliminary dose-response experiments we determined that 5 μg of endotoxin induced a strong (70–80% maximal) mammary neutrophil response. Thus, in the reported experiments mastitis was induced by infusion of 5 μg of endotoxin or carrier medium alone (saline; 3 ml volumes) into the teat cisterns of nonlactating Holstein dairy cows, and 15 h later the infiltrates were recovered from the cisterns by lavage with 30 ml HBSS. The cells from the BALF and teat cistern wash fluids were sedimented by centrifugation and differential counts performed. Untreated and CXCL8-depleted (below) wash fluids were assessed for their chemokine content by ELISA (CXCL8 only) and chemotaxis assays.

Neutrophil chemotaxis assays. Microchemotaxis assays were run in duplicate modified Boyden microchemotaxis chambers using polyvinylpyrrolidone-free 5 μm pore-size polycarbonate filters, in accordance with known methods (ref. 26, 29). For each sample, the numbers of cells that had migrated into the membranes over 20–30 min were enumerated by direct counting of at least nine 40.times. objective fields, and the results expressed as the mean number of cells/40× field (+/− SEM). The chemoattractants included bovine or human CXCL8, human CXCL5 and CXCL1, pneumonic mannheimiosis BALF and mastitis lavage fluids (diluted 1:10–1:80 in HBSS), while the antagonists comprised mouse anti-ovine CXCL8 antibody 8M6 (generously provided by Dr. P. Wood, CSIRO, Australia) or the $CXCL8_{(3-74)}$K11R analogues. In some assays we preincubated the samples with the antibodies (5 μg/ml) for 60 min on ice (ref. 30). In others we generated CXCL8-specific immunoaffinity matrices with the 8M6 antibodies and protein-A-Sepharose beads and used these in excess to absorb the samples (ref. 8, 31); the extent of CXCL8 depletion was confirmed by ELISA of the treated samples. For assays with the recombinant antagonists, the inhibitors were mixed directly with the samples immediately prior to testing.

CXCL8 ELISA. For our ELISA, MAb 8M6 was used as the capture antibody, rabbit antiovine CXCL8 antiserum (also from P. Wood, CSIRO) as the secondary antibody, and HRPconjugated anti-rabbit Ig, and TMB as the detection system, as noted in Caswell et al. (ref. 8). Serial dilutions of each sample were assayed in triplicate, and each assay included a recombinant bovine CXCL8 standard curve.

$CXCL8_{(3-74)}$K11R/G31P blockade of endotoxin responses in vivo. We used a sequential series of 15 h skin tests to test the ability of $CXCL8_{(3-73)}$K11R/G31P to block endotoxininduced inflammatory responses in vivo. For each test, we challenged 2 week-old healthy Holstein cows intradermally with 1 μg endotoxin in 100 μl saline, then 15 h later took 6 mm punch biopsies under local anaesthesia (lidocaine) and processed these for histopathology (ref. 31). Following the first (internal positive control) test, we injected each animal subcutaneously, intramuscularly, or intravenously with $CXCL8_{(3-74)}$K11R/G31P (75 μg/kg) in saline, then challenged them again with endotoxin, as above. The animals were challenged a total of 4 times with endotoxin, such that 15 h reaction site biopsies were obtained at 0, 16, 48, and 72 h post-treatment. The biopsies were processed by routine methods to 6 .mu. paraffin sections, stained with Giemsa solution, and examined in a blinded fashion at 400− magnification (ref. 31, 32). The mean numbers of neutrophils per 40× objective microscope field were determined at three different depths within the skin, the papillary (superficial), intermediate, and reticular (deep) dermis.

Statistical analyses. Multi-group data were analyzed by ANOVA and post-hoc Fisher protected Least Significant Difference (PLSD) testing, while two-group comparisons were made using the students t-test (two-tailed). The results are expressed as the mean +/− SEM.

Results $CXCL8_{(3-74)}$K11R/G31P competitively inhibits CXCL8 binding to neutrophils. We surveyed the ability of each $CXCL8_{(3-74)}$K11R analogue to bind to the CXCL8 receptors on neutrophils, and thereby compete with CXCL8 as a ligand. In our initial surveys, we employed $^{biot}$CXCL8 binding inhibition assays, incubating the cells with the analogues (10 ng/ml) for 2 h at 4° C. prior to exposure to $^{biot}$CXCL8 (1 μg/ml). This level of CXCL8 approximates those found in the lung tissues of sheep with experimental pneumonic mannheimiosis (ref. 33). We found that $CXCL8_{(3-74)}$K11R/G31P was a potent antagonist of CXCL8 binding in this assay (FIG. 1), such that 10 ng/ml of $CXCL8_{(3-74)}$K11R/G31P blocked 95% of subsequent $^{biot}$CXCL8 binding to the cells. When tested at this dose, $CXCL8_{(3-74)}$K11R/P32G blocked only 48% of CXCL8 binding, while unlabeled CXCL8 itself competitively inhibited 30% of $^{biot}$CXCL8 binding. Introduction into $CXCL8_{(3-74)}$K11R/G31P or $CXCL8_{(3-74)}$K11R/P32G of additional amino acid substitutions at Thr12 and His13 substantially reduced the antagonist activities of the analogues (FIG. 1). This data clearly suggests that pre-incubation of neutrophils with $CXCL8_{(3-74)}$K11R/G31P strongly down-regulates subsequent binding of CXCL8.

In order to more finely map the ability of $CXCL8_{(3-74)}$K11R/G31 to inhibit the binding of CXCL8, in our next set of experiments we simultaneously exposed the cells to $^{125}$ICXCL8 and varying doses of $CXCL8_{(3-74)}$K11R/G31P or unlabeled CXCL8. We found that $CXCL8_{(3-74)}$K11R/G31P was about two orders of magnitude more effective than wildtype CXCL8 in inhibiting the binding of 20 pM $^{125}$I-CXCL8 to the cells (FIG. 1). The concentration for inhibiting 50% of labelled ligand binding ($IC_{50}$) was 120 pM for unlabelled CXCL8, and 4 pM for $CXCL8_{(3-74)}$K11R/G31P. This data suggests that $CXCL8_{(3-74)}$K11R/G31P is a very potent competitive inhibitor of CXCL8 binding to neutrophils.

Figure 2:
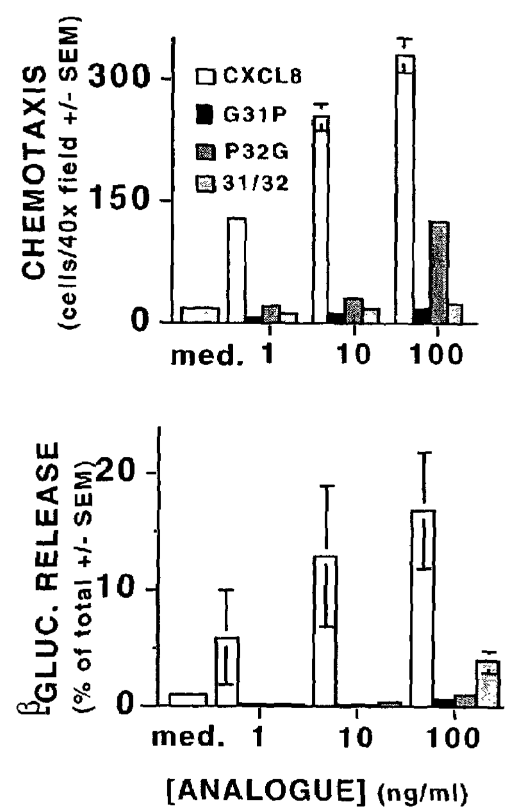
FIG. 2. $CXCL8_{(3-74)}$K11R/G31P is not an agonist of neutrophil chemoattraction responses or β-glucuronidase release. CXCL8 and the G31P, P32G, or combined G31P/P32G analogues of $CXCL8_{(3-74)}$K11R were tested for their neutrophil agonist activities, using freshly purified bovine peripheral blood neutrophils. (upper panel) The chemotactic responses to each protein were tested in 30 min micro-chemotaxis assays and the results expressed as the mean (+/− SEM) number of cells/40× objective microscope field, as outlined in the methods section. Both the G31P and G31P/P32G analogues displayed little discernable chemotactic activity, while the P32G analogue stimulated substantial responses at 100 ng/ml. (lower panel) The neutrophils were exposed to varying doses of each analogue for 30 min, then the cellular secretion products were assayed for β-glucuronidase using the chromogenic substrate p-nitrophenyl—βD-glucuronide, as presented in the methods section. The total cellular stores of β-glucuronidase were determined from aliquots of cells lysed with Triton-X-100. The enzyme release with each treatment is expressed as the percent of the total cellular stores. None of the analogues had substantial agonist activity, although CXCL8 itself did induce significant enzyme release. The positive control treatment with phorbol-12,13-myristate acetate and calcium ionophore A23187 induced 42+/−6% enzyme release.

$CXCL8_{(3-74)}$K11R/G31P does not display neutrophil agonist activities. While $CXCL8_{(3-74)}$K11R/G31P was certainly a high affinity ligand for the neutrophil CXCL8 receptors, it would equally well do so as an agonist or an antagonist. Thus our next experiments addressed the potential agonist activities of the $CXCL8_{(3-74)}$K11R analogues we generated, as measured by their abilities to chemoattract these cells or induce release of the neutrophil granule hydrolytic enzyme β-glucuronidase in vitro (FIG. 2). We found that even at 100 ng/ml, $CXCL8_{(3-74)}$K11R/G31P was a poor chemoattractant, inducing 13.9+/−4% or 5.4+/−2% of the responses induced by 1 or 100 ng/ml CXCL8 ($p<0.001$), respectively. At 100 ng/ml, the $CXCL8_{(3-73)}$K11R/P32G analogue induced a response that was fairly substantial (38.3+/−2% of the CXCL8 response), while the combined $CXCL8_{(3-74)}$K11R/G31P/P32G analogue also was not an effective chemoattractant. When we assessed their abilities to induce -glucuronidase release, we found that none of the $CXCL8_{(3-74)}$K11R analogues was as effective as CXCL8 in inducing mediator release. Indeed, we found only background release with any of them at 10 ng/ml, and at 100 ng/ml only $CXCL8_{(3-74)}$K11R/G31P/P32G induced significant neutrophil responses (FIG. 2). Given the combined CXCL8 competitive inhibition and neutrophil agonist data, from this point on we focused our attention on $CXCL8_{(3-74)}$K11R/G31P.

Figure 3:
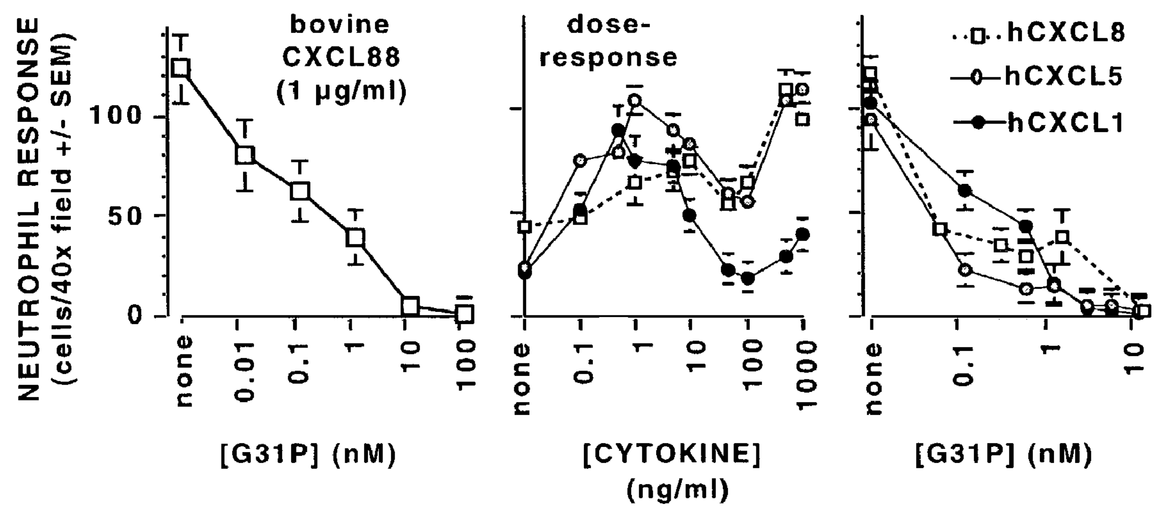
FIG. 3 $CXCL8_{(3-74)}$K11R-G31P is a highly effective antagonist ELR-CXC chemokine-medicated neutrophil chemoattraction. The ability of $CXCL8_{(3-74)}$K11R/G31P to block chemotactic responses of bovine neutrophils to several ELR-CXC chemokines was measured using 20 min micro-chemotaxis assays. (left panel) The cells were simultaneously exposed to CXCL8 (1 μg/ml) and varying concentrations of the analogue. The number of cells that responded to the CXCL8 was assessed by direct counting of the chemotaxis assay membranes, as in FIG. 2. $CXCL8_{(3-74)}$K11R/G31P was a highly effective competitive inhibitor of the cell's responses to CXCL8. (middle panel) Dose-response curves for chemoattraction of bovine neutrophils by human CXCL1, CXCL5, or CXCL8. Each chemokine displayed a biphasic activity pattern, with maxima at 1–10 ng/ml and at 1 μg/ml. (right panel) The ability of $CXCL8_{(3-74)}$K11R/G31P to block the cell's responses to 1 ng/ml of human CXCL5 or CXCL1 or 10 ng/ml of human CXCL8 was assessed as above. $CXCL8_{(3-74)}$K11R/G31P effectively antagonized each ELR-CXC chemokine, with complete inhibition being achieved with from 3–20 nM $CXCL8_{(3-74)}$K11R/G31P.

$CXCL8_{(3-74)}$K11R/G31P blocks neutrophil chemotactic responses to both CXCR1 and CXCR2 ligands. The most pathogenic effect of inappropriate $ELR^+$ chemokine expression is the attraction of inflammatory cells into tissues. Thus, we next assessed the impact of $CXCL8_{(3-74)}$K11R/G31P on the chemotactic responses of neutrophils to high doses of CXCL8 (FIG. 3). As predicted from our in vivo observations in sheep and cattle (ref. 33), 1 μg/ml (129 nM) CXCL8 was very strongly chemoattractive, but even very low doses of $CXCL8_{(3-74)}$K11R/G31P ameliorated this response. The addition of 12.9 pM $CXCL8_{(3-74)}$K11R/G31P reduced the chemotactic response of the cells by 33%. The $IC_{50}$ for $CXCL8_{(3-74)}$K11R/G31P under these conditions was 0.11 nM, while complete blocking of this CXCL8 response was achieved with 10 nM $CXCL8_{(3-74)}$K11R/G31P.

When we tested the efficacy of $CXCL8_{(3-74)}$K11R/G31P in blocking responses to more subtle bovine CXCL8 challenges, we also extended the study to assess the ability of $CXCL8_{(3-74)}$K11R/G31P to block neutrophil responses to human CXCL8 as well as to the human CXCR2-specific ligands CXCL1 and CXCL5. Each of these is expressed in the affected tissues of pancreatitis (ref. 34) or ARDS (ref. 3) patients at 1–10 ng/ml. We found that bovine neutrophils were responsive to 1 ng/ml hCXCL1 or hCXCL5, and similarly responsive to 10 ng/ml hCXCL8 (FIG. 3), so we employed these doses to test the effects of $CXCL8_{(3-74)}$K11R/G31P on neutrophil responses of these ligands. The neutrophil responses to hCXCL1 and hCXCL5 were reduced to 50% by 0.26 and 0.06 nM $CXCL8_{(3-74)}$K11R/G31P, respectively, while their responses to hCXCL8 were 50% reduced by 0.04 nM $CXCL8_{(3-74)}$K11R/G31P (FIG. 3). This data indicates that $CXCL8_{(3-74)}$K11R/G31P can antagonize the actions of multiple members of the ELR-CXC subfamily of chemokines.

$CXCL8_{(3-74)}$K11R/G31P is an effective in vitro antagonist of the neutrophil chemokines expressed in bacterial pneumonia or mastitis lesions. We wished to test the extent to which our antagonist could block the array of neutrophil chemoattractants expressed within complex inflammatory environments in vivo. Thus, we chose two diseases in which chemokine-driven neutrophil activation contributes importantly to the progression of the pathology, mastitis and pneumonic mannheimiosis. We utilized an endotoxin model of mastitis (ref. 35), in which we infused 5 μg of endotoxin/teat cistern and 15 h later lavaged each cistern. Neutrophils comprised 82 and 6%, respectively, of the cells from endotoxin and saline-control cisterns, with the bulk of the remaining cells comprising macrophages. The diluted (1:10) wash fluids induced strong in vitro neutrophil chemotactic responses, and the addition of anti-CXCL8 antibodies to the samples maximally reduced these by 73+/−8% (FIG. 4A), relative to the medium control. On the other hand, the addition of 1 ng/ml of $CXCL8_{(3-74)}$K11R/G31P to the samples reduced their chemotactic activity by 97+/−3%.

Figure 4:
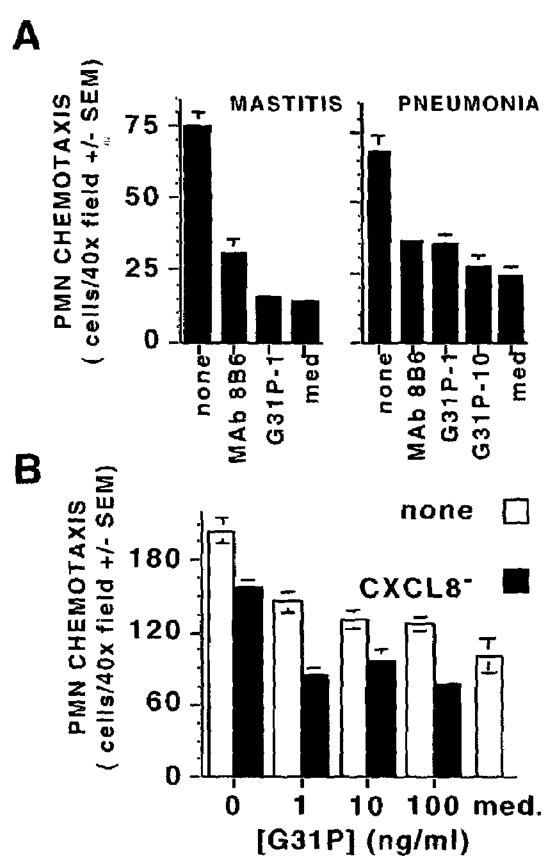
FIG. 4. $CXCL8_{(3-74)}$K11R-G31P blocks the activities of CXCL8 and non-CXCL8 chemoattractants expressed within pneumonic airways or in endotoxin-induced mastitis. The effects of monoclonal anti-IL8 antibody 8B6 or $CXCL8_{(3-74)}$K11R-G31P on neutrophil responses to the chemoattractants expressed within the airways of animals with pneumonic pasteurellosis or in the mammary cisterns of cattle with endotoxin-induced mastitis were assessed as in FIG. 3. (A) Diluted (1:10) bronchoalveolar lavage fluids (BALF) from lesional lung lobes of pneumonic cattle (PNEUMONIA) or teat cistern lavage fluids from cattle with mastitis (MASTITIS) were tested as is (none) or after treatment with either anti-CXCL8 MAb 8B6 (5 μg/ml) or $CXCL8_{(3-74)}$K11R/G31P (G31P; 1 or 10 ng/ml) for their chemotactic activities compared to medium alone. With both samples, the Mab 8B6 antibodies by themselves neutralized 74% of the chemotactic activities in the samples, while $CXCL8_{(3-74)}$K11R/G31P reduced the responses by 93–97%. (B) In order to confirm these results using an alternate strategy, we next absorbed lesional BAL fluids with monoclonal antibody 8B6-immunoaffinity matrices, removing >99% of their content of CXCL8, then tested both their residual chemotactic activities and the ability of $CXCL8_{(3-74)}$K11R/G31P to antagonize these residual non-CXCL8 chemotactic activities. There was a dose-dependent inhibition of the total and residual chemotactic activities in the samples, indicating that both CXCL8 and non-CXCL8 chemoattractants are expressed in these lesions.

Neutrophils also comprised 93+/−12% of the cells recovered from the BALF of cattle with advanced pneumonic mannheimiosis. When tested in vitro, these samples too were strongly chemotactic for neutrophils, and the addition of anti-CXCL8 antibodies maximally reduced their neutrophil chemotactic activities by 73+/−5% (FIG. 4A). Treatment of these BALF samples with 1 or 10 ng/ml of $CXCL8_{(3-74)}$K11R/G31P reduced the neutrophil responses by 75+/−9 or 93+/−9%, respectively, relative to the medium controls. This data suggests that $CXCL8_{(3-74)}$K11R/G31P blocks the actions of CXCL8 and non-CXCL8 chemoattractants in these samples.

In order to confirm these observations using an alternate strategy, we next depleted bacterial pneumonia BALF samples of CXCL8 using immunoaffinity matrices, then assessed the efficacy of $CXCL8_{(3-74)}$K11R/G31P in blocking the residual neutrophil chemotactic activities in the samples (FIG. 4B). The untreated lesional BALF samples contained 3,215+/−275 pg/ml CXCL8, while the immunoaffinity-absorbed BALF contained 24+/−17 pg/ml CXCL8. In this series of experiments the neutrophil response to the CXCL8-depleted BALF samples was 65.4+/−4% of their responses to the unabsorbed samples. It is known that CXCL8 can contribute as little as 15% of the neutrophil chemotactic activities in pneumonic mannheimiosis BALF obtained from an array of clinical cases (ref. 9). Whereas the CXCL8 depletion treatments were 99% effective in removing CXCL8, there remained in these samples substantial amounts of neutrophil chemotactic activities, and the addition of 1 ng/ml $CXCL8_{(3-74)}$K11R/G31P fully abrogated their cumulative effects (FIG. 4B). This data unequivocally confirmed that $CXCL8_{(3-74)}$K11R/G31P also antagonizes the spectrum of non-IL-8 chemoattractants expressed in these samples.

Figure 5:
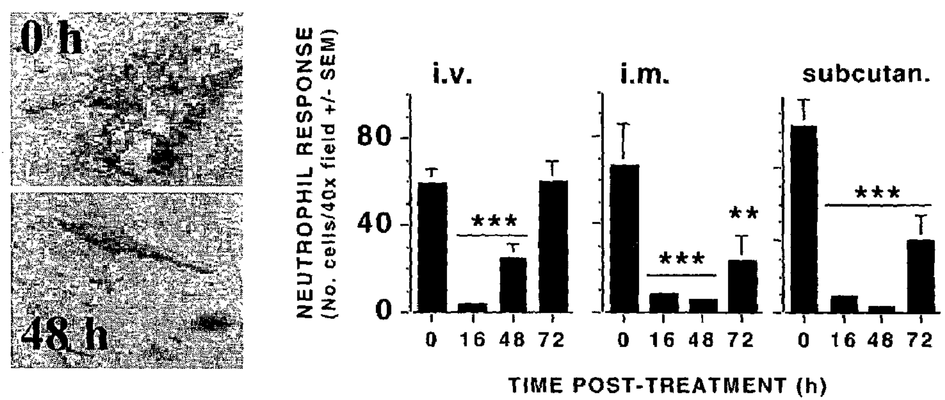
FIG. 5. $CXCL8_{(3-74)}$K11R-G31P can ablate endotoxin-induced inflammatory responses in vivo. Two week-old Holstein calves were tested for their neutrophilic inflammatory responses to intradermal endotoxin (1 μg/site) challenge before and at various time after intravenous (i.v.), subcutaneous (subcutan.), or intramuscular (i.m.) injection of $CXCL8_{(3-74)}$K11R-G31P (75 μg/kg). Fifteen hour endotoxin reaction site biopsies were obtained at 0, 16, 48 and 72 h post-treatment and processed for histopathologic assessment of the neutrophil response, as determined by counting the numbers of neutrophils in nine 40× objective microscope fields per section. (left panel) Photomicrographs of the tissue responses to endotoxin challenge around blood vessels within the reticular dermis prior to (0 h) and 48 h post-treatment. Large numbers of neutrophils accumulated around the vasculature within the reticular dermis in the pre-, but not post-treatment tissues. (B) Graphic presentation of the neutrophil responses to endotoxin challenge either before (0 h) or after (16, 48, 72 h) $CXCL8_{(3-74)}$K11R-G31P delivery by each route.  or *=p 0.01 or 0.001, respectively, relative to the internal control pretreatment responses.

CXCL8$_{(3-74)}$K11R/G31P is highly efficacious in blocking endotoxin-induced neutrophilic inflammation in vivo. In our last experiments, we assessed the ability of CXCL8$_{(3-74)}$K11R/G31P to block endotoxin-induced inflammatory responses in the skin of cattle, as well as the time-frames over which it was effective. The animals were challenged intradermally with 1 μg bacterial endotoxin 15 h before (internal positive control response), or at three different times after, intravenous, subcutaneous or intramuscular injection of CXCL8$_{(3-74)}$K11R/G31P (75 μg/kg). Thus, punch biopsies of 15 h endotoxin reaction sites were taken 15 min before treatment and at 16, 48 and 72 h after injection of the antagonist into each animal, and the numbers of infiltrating neutrophils were determined in a blinded fashion for the papillary (superficial), intermediate and reticular dermis of each biopsy. Prior to the antagonist treatments, strong neutrophilic inflammatory responses were evident at the endotoxin challenge sites in each animal (FIG. 5). Within the biopsies, the responses in the papillary dermis were mild in all animals (data not shown) and became progressively more marked with increasing skin depth, such that maximal inflammation (neutrophil infiltration) was observed around the blood vessels in the reticular dermis (FIG. 5A). Following the CXCL8$_{(3-74)}$K11R/G31P treatments, the inflammatory responses observed within the 16 h biopsies were 88–93% suppressed, while those in the 48 h biopsies were 57% (intravenous) to 97% (intradermal) suppressed, relative to their respective pretreatment responses. By 72 h post-treatment the effects of the intravenously administered antagonist had worn off, while the endotoxin responses in the intradermally and subcutaneously treated cattle were still 60% suppressed. This data clearly indicates that CXCL8$_{(3-74)}$K11R/G31P is a highly effective antagonist of endotoxin-induced inflammatory responses in vivo, that these effects can last for 2–3 days, and that the route of delivery markedly affects the pharmacokinetics of this novel antagonist.

Figure 6:
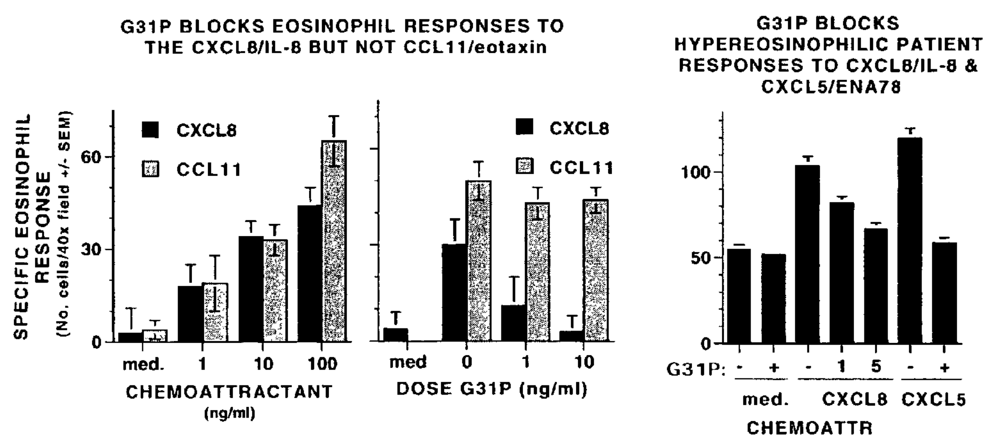
FIG. 6 Eosinophils purified from the blood of atopic asthmatic or atopic non-asthmatic donors (left panels) or a subject with a hypereosinophilia (right panel) were assessed for their responses to recombinant human CXCL8, CXCL5, or CCL11, in the presence or absence of the indicated doses of recombinant bovine $CXCL8_{(3-74)}$K11R/G31P (G31P). Low doses of G31P were able to block the responses of these cells to each of the CXCR1 and CXCR2 ligands, but had no effect on the eosinophil's responses to the unrelated CCR3 ligand CCL11/eotaxin.
Figure 7:
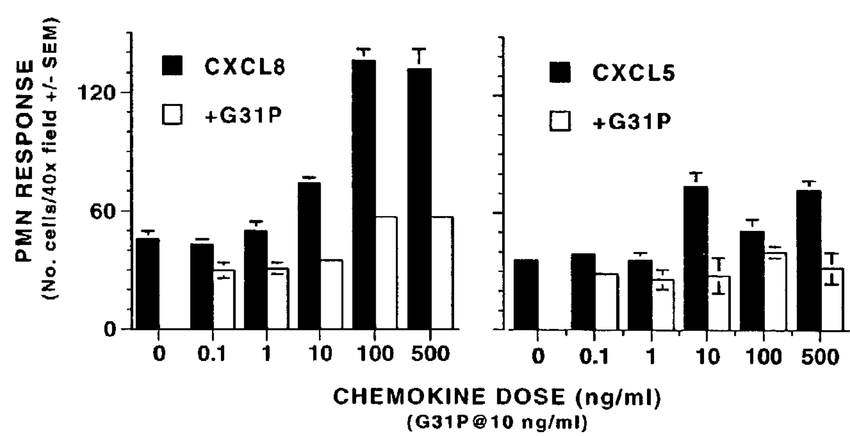
FIG. 7 Neutrophils from the peripheral blood of a healthy donor were tested for their responses to recombinant human CXCL8 or CXCL5 in the presence or absence of bovine $CXCL8_{(3-74)}$K11R/G31P (G31P; 10 ng/ml). G31P blocked the neutrophil's responses to both ligands.

We have found that G31 antagonizes also the chemotactic effects of the human ELR-CXC chemokines CXCL8/IL-8 and CXCL5/ENA-78 on human neutrophils. Thus, the chemotactic activities of 0.1 to 500 ng/ml of either CXCL8 (FIG. 6, left panel) or CXCL5/ENA-78 (FIG. 6, right panel) were essentially completely blocked by the addition of 10 ng/ml of our antagonist to the chemotaxis assays. Similarly, G31P blocked the chemotactic effects of CXCL8 for CXCR1/CXCR2-positive eosinophils. We and others have found that eosinophils from atopic or asthmatic subjects express both ELR-CXC chemokine receptors, and are responsive to CXCL8 (FIG. 7, left panel). The chemotactic effects of 100 ng/ml CXCL8, but not the CCR3 ligand CCL11/eotaxin, on purified peripheral blood eosinophils of an mildly atopic, non-asthmatic donor (‰99% purity) were completely abrogated by the addition of 10 ng/ml G31P to the chemotaxis assays (FIG. 7, middle panel). When tested against purified eosinophils from a hypereosinophilic patient (FIG. 7, right panel), G31P was neutralized the responses of these cells to either CXCL8/IL-8 or CXCL5/ENA-78.

This data clearly indicates that bovine G31P is an effective antagonist of the bovine ELR-CXC chemokines expressed in vivo in response to endotoxin challenge, but also can fully antagonize neutrophil and eosinophil ELR-CXC chemokine receptor responses to CXCL8 and CXCL5, known ligands for both the CXCR1 and CXCR2.

TABLE 1

PCR primers employed for the generation of each CXCL8 analogue.

| CXCL8$_{(3-74)}$ K11R ANALOGUE | upstream primer (5'–3' orientation) | downstream primer (5'–3' orientation) |
|---|---|---|
| T12S/H13F | CA GAA CTT CGA TGC CAG TGC ATA AGA TCA TTT TCC ACA CCT TTC C | G AA AGG TGT GGA AAA TGA TCT TAT GCA CTG GCA TCG AAG TTC TG |
| G31P | GAG AGT TAT TGA GAG TCC GCC ACA CTG TGA AAA TTC AGA AAT C | GAT TTC TGA ATT TTC ACA GTG TGG CGG ACT CTC AAT AAC TCT C |
| P32G | GAG AGT TAT TGA GAG TGG GGG ACA CTG TGA AAA TTC AGA AAT C | GAT TTC TGA ATT TTC ACA GTG TCC CCC ACT CTC AAT AAC TCT C |
| G31P/P32G | GAG AGT TAT TGA GAG TCC GGG ACA CTG TGA AAA TTC AGA AAT C | GAT TTC TGA ATT TTC CAC GTG TCC CGG ACT CTC AAT AAC TCT C |

DISCUSSION

We demonstrated herein that CXCL8$_{(3-74)}$K11R/G31P is a high affinity antagonist of multiple ELR-CXC chemokines. In vitro, this antagonist effectively blocked all of the neutrophil chemotactic activities expressed in mild to intense inflammatory lesions within two mucosal compartments (lungs, mammary glands), and up to 97% blocked endotoxin-induced inflammatory responses in vivo. We identified CXCL8 as a major chemoattractant in the pneumonia and mastitis samples, but also demonstrated that 35% of the activity in the bacterial pneumonia samples was due to non-CXCL8 chemoattractants that were also effectively antagonized by CXCL8$_{(3-74)}$K11R/G31P. Based on studies of inflammatory responses in rodents (ref. 18, 19), cattle (ref. 8), and humans (ref. 3), it is clear that these samples could contain numerous ELR$^+$ CXC chemokines (e.g., CXCL5, and CXCL8) to which CXCL8$_{(3-74)}$K11R/G31P has an antagonistic effect.

REFERENCES

1. Baggiolini, M. 1998. Chemokines and leukocyte traffic. *Nature*. 392:565–568.
2. Sekido, N., N. Mukaida, A. Harada, I. Nakanishi, Y. Watanabe, and K. Matsushima. 1993. Prevention of lung reperfusion injury in rabbits by a monoclonal antibody against interleukin-8. *Nature*. 365:654–657.
3. Villard, J., F. Dayer Pastore, J. Hamacher, J. D. Aubert, S. Schlegel Haueter, and L. P. Nicod. 1995. GRO alpha and interleukin-8 in *Pneumocystis carinii* or bacterial pneumonia and adult respiratory distress syndrome. Am. J. Respir. Crit. Care Med. 152:1549–1554.
4. Mukaida, N., T. Matsumoto, K. Yokoi, A. Harada, and K. Matsushima. 1998. Inhibition of neutrophil-mediated acute inflammation injury by an antibody against interleukin-8 (IL-8). Inflamm. Res. 47 (suppl. 3):S151–157.
5. Harada, A., N. Mukaida, and K. Matsushima. 1996. Interleukin 8 as a novel target for intervention therapy in acute inflammatory diseases. Inflamm. Res. 2:482–489.
6. Walley, K. R., N. W. Lukacs, T. J. Standiford, R. M. Strieter, and S. L. Kunkel. 1997. Elevated levels of macrophage inflammatory protein 2 in severe murine peritonitis increase neutrophil recruitment and mortality. Infect. Immun. 65:3847–3851.

7. Slocombe, R., J. Malark, R. Ingersoll, F. Derksen, and N. Robinson. 1985. Importance of neutrophils in the pathogenesis of acute pneumonic pasteurellosis in calves. Am. J. Vet. Res. 46:2253.

8. Caswell, J. L., D. M. Middleton, S. D. Sorden, and J. R. Gordon. 1997. Expression of the neutrophil chemoattractant interleukin-8 in the lesions of bovine pneumonic pasteurellosis. Vet. Pathol. 35:124–131.

9. Caswell, J. L., D. M. Middleton, and J. R. Gordon. 2001. The importance of interleukin-8 as a neutrophil chemoattractant in the lungs of cattle with pneumonic pasteurellosis. Canad. J. Vet. Res. 65:229–232.

10. Baggiolini, M., and B. Moser. 1997. Blocking chemokine receptors. J. Exp. Med. 186:1189–1191.

11. Ahuja, S. K., and P. M. Murphy. 1996. The CXC chemokines growth-regulated oncogene (GRO) alpha, GRObeta, GROgamma, neutrophil-activating peptide-2, and epithelial cell derived neutrophil-activating peptide-78 are potent agonists for the type B, but not the type A, human interleukin-8 receptor. J. Biol. Chem. 271:20545–20550.

12. Loetscher, P., M. Seitz, I. Clark Lewis, M. Baggiolini, and B. Moser. 1994. Both interleukin-8 receptors independently mediate chemotaxis. Jurkat cells transfected with IL-8R1 or IL-8R2 migrate in response to IL-8, GRO alpha and NAP-2. FEBS Lett. 341:187–192.

13. Wuyts, A., P. Proost, J. P. Lenaerts, A. Ben Baruch, J. Van Damme, and J. M. Wang. 1998. Differential usage of the CXC chemokine receptors 1 and 2 by interleukin-8, granulocyte chemotactic protein-2 and epithelial-cell-derived neutrophil attractant-78. Eur. J. Biochem. 255:67–73.

14. Richardson, R., B. Pridgen, B. Haribabu, H. Ali, and R. Snyderman. 1998. Differential cross-regulation of the human chemokine receptors CXCR1 and CXCR2. Evidence for time-dependent signal generation. J. Biol. Chem. 273:23830–23836.

15. McColl, S. R., and I. Clark Lewis. 1999. Inhibition of murine neutrophil recruitment in vivo by CXC chemokine receptor antagonists. J. Immunol. 163:2829–2835.

16. Jones, S. A., M. Wolf, S. Qin, C. R. Mackay, and M. Baggiolini. 1996. Different functions for the interleukin 8 receptors (IL-8R) of human neutrophil leukocytes: NADPH oxidase and phospholipase D are activated through IL-8R1 but not IL-8R2. Proc. Natl. Acad. Sci. U. S. A. 93:6682–6686.

17. White, J. R., J. M. Lee, P. R. Young, R. P. Hertzberg, A. J. Jurewicz, M. A. Chaikin, K. Widdowson, J. J. Foley, L. D. Martin, D. E. Griswold, and H. M. Sarau. 1998. Identification of a potent, selective non-peptide CXCR2 antagonist that inhibits interleukin-8-induced neutrophil migration. J. Biol. Chem. 273:10095–10098.

18. Tateda, K., T. A. Moore, M. W. Newstead, W. C. Tsai, X. Zeng, J. C. Deng, G. Chen, R. Reddy, K. Yamaguchi, and T. J. Standiford. 2001. Chemokine-dependent neutrophil recruitment in a murine model of Legionella pneumonia: potential role of neutrophils as immunoregulatory cells. Infect. Immun. 69:2017–2024.

19. Tsai, W. C., R. M. Strieter, B. Mehrad, M. W. Newstead, X. Zeng, and T. J. Standiford. 2000. CXC chemokine receptor CXCR2 is essential for protective innate host response in murine Pseudomonas aeruginosa pneumonia. Infect. Immun. 68:4289–4296.

20. Goodman, R. B., R. M. Strieter, C. W. Frevert, C. J. Cummings, P. Tekamp Olson, S. L. Kunkel, A. Walz, and T. R. Martin. 1998. Quantitative comparison of C-X-C chemokines produced by endotoxin-stimulated human alveolar macrophages. Am. J. Physiol. 275:L87–95.

21. Nufer, O., M. Corbett, and A. Walz. 1999. Amino-terminal processing of chemokine ENA-78 regulates biological activity. Biochem. 38:636–642.

22. Wuyts, A., A. D'Haese, V. Cremers, P. Menten, J. P. Lenaerts, A. De Loof, H. Heremans, P. Proost, and J. Van Damme. 1999. NH2- and COOH-terminal truncations of murine granulocyte chemotactic protein-2 augment the in vitro and in vivo neutrophil chemotactic potency. J. Leukoc. Biol. 163:6155–6163.

23. Clark Lewis, I., B. Dewald, M. Loetscher, B. Moser, and M. Baggiolini. 1994. Structural requirements for interleukin-8 function identified by design of analogs and CXC chemokine hybrids. J. Biol. Chem. 269:16075–16081.

24. Li, F., and J. R. Gordon. 2001. IL-$8_{(3-73)}$K11R is a high affinity agonist of the neutrophil CXCR1 and CXCR2. Biochem. Biophys. Res. Comm. 286:595–600.

25. Moser, B., B. Dewald, L. Barella, C. Schumacher, M. Baggiolini, and I. Clark Lewis. 1993. Interleukin-8 antagonists generated by N-terminal modification. J. Biol. Chem. 268:7125–7128.

26. Caswell, J. L., D. M. Middleton, and J. R. Gordon. 1998. Production and functional characterization of recombinant bovine interleukin-8 as a neutrophil-activator and specific chemoattractant in vitro and in vivo. Vet. Immunol. Immunopath. 67:327–340.

27. Coligan, J., A. Kruisbeek, D. Margulies, E. Shevach, and W. Strober. 1994. Current Protocols in Immunology. John Wiley & Sons, New York.

28. Waller, K. P. 1997. Modulation of endotoxin-induced inflammation in the bovine teat using antagonists/inhibitors to leukotrienes, platelet activating factor and interleukin 1 beta. Vet. Immunol. Immunopathol. 57:239–251.

29. Cairns, C. M., J. R. Gordon, F. Li, M. E. Baca-Estrada, T. N. Moyana, and J. Xiang. 2001. Lymphotactin expression by engineered myeloma tumor cells drives tumor regression. Mediation by CD4+ and CD8+ T cells and neutrophils expressing XCR1 receptors. J. Immunol. 167: 57–65.

30. Gordon, J. R. 2000. TGFb and TNFa secretion by mast cells stimulated via the FceRI activates fibroblasts for high level production of monocyte chemoattractant protein-1. Cell Immunol. 201:42–49.

31. Gordon, J. R., and S. J. Galli. 1994. Promotion of mouse fibroblast collagen gene expression by mast cells stimulated via the FceRI. Role for mast cell-derived transforming growth factor-b and tumor necrosis factor-a. J. Exp. Med. 180:2027–2037.

32. Gordon, J. R. 2000. Monocyte chemoattractant protein-1 (MCP-1) expression during cutaneous allergic responses in mice is mast cell-dependent and largely mediates monocyte recruitment. J. Allergy Clin. Immunol. 106: 110–116.

33. Caswell, J. L. 1998. The role of interleukin-8 as a neutrophil chemoattractant in bovine bronchopneumonia. Ph.D. thesis, Department of Veterinary Pathology, University of Saskatchewan. 241 pg.

34. Hochreiter, W. W., R. B. Nadler, A. E. Koch, P. L. Campbell, M. Ludwig, W. Weidner, and A. J. Schaeffer. 2000. Evaluation of the cytokines interleukin-8 and epithelial neutrophil activating peptide-78 as indicators of inflammation in prostatic secretions. Urology. 56:1025–1029.

35. Persson, K., I. Larsson, and C. Hallen Sandgren. 1993. Effects of certain inflammatory mediators on bovine neutrophil migration in vivo and in vitro. Vet. Immunol. Immunopathol. 37:99–112.

36. Gray, G. D., K. A. Knight, R. D. Nelson, and M. Herron, J. 1982. Chemotactic requirements of bovine leukocytes. Am. J.Vet. Res. 43:757–759.

37. Fernandez, H. N., P. M. Henson, A. Otani, and T. E. Hugli. 1978. Chemotactic response to human C3a and C5a anaphylatoxins. I. Evaluation of C3a and C5a leukotaxis in vitro and under stimulated in vivo conditions. J. Immunol. 120:109–115.

38. Riollet, C., P. Rainard, and B. Poutrel. 2000. Differential induction of complement fragment C5*a* and inflammatory cytokines during intramammary infections with *Escherichia coli* and *Staphylococcus aureus*. Clin. Diagn. Lab Immunol. 7:161–167.

39. Shuster, D. E., M. E. Kehrli, Jr., P. Rainard, and M. Paape. 1997. Complement fragment C5*a* and inflammatory cytokines in neutrophil recruitment during intramammary infection with *Escherichia coli*. Infect. Immun. 65:3286–3292.

40. Bless, N. M., R. L. Warner, V. A. Padgaonkar, A. B. Lentsch, B. J. Czermak, H. Schmal, H. P. Friedl, and P. A. Ward. 1999. Roles for C-X-C chemokines and C5a in lung injury after hindlimb ischemia-reperfusion. Am. J. Physiol. 276:L57–63.

41. Ember, J. A., S. D. Sanderson, T. E. Hugli, and E. L. Morgan. 1994. Induction of interleukin-8 synthesis from monocytes by human C5a anaphylatoxin. Am. J. Pathol. 144:393–403.

42. Fisher, C., G. Slotman, S. Opal, J. Pribble, R. Bone, G. Emmanuel, D. Ng, D. Bloedow, and M. Catalano. 1994. Initial evaluation of human recombinant interleukin-1 receptor antagonist in the treatment of sepsis syndrome: a randomized, open-label, placebocontrolled multicenter trial. The IL-1RA Sepsis Syndrome Study Group. Crit. Care Med. 22:11–21.

43. Verbon, A., P. E. Dekkers, T. ten Hove, C. E. Hack, J. Pribble, T. Turner, S. Souza, T. Axtelle, F. Hoek, -.S.-J. van Deventer, and T. van der Poll. 2001. IC14, an anti-CD 14 antibody, inhibits endotoxin-mediated symptoms and inflammatory responses in humans. J.Immunol. 166:3599–3605.

44. Clark Lewis, I., K. S. Kim, K. Rajarathnam, J. H. Gong, B. Dewald, B. Moser, M. Baggiolini, and B. D. Sykes. 1995. Structure-activity relationships of chemokines. J. Leukoc. Biol. 57:703–711.

45. Jones, S. A., B. Dewald, I. Clark Lewis, and M. Baggiolini. 1997. Chemokine antagonists that discriminate between interleukin-8 receptors. Selective blockers of CXCR2. J. Biol. Chem. 272:16166–16169.

46. Hang, L., B. Frendeus, G. Godaly, and C. Svanborg. 2000. Interleukin-8 receptor knockout mice have subepithelial neutrophil entrapment and renal scarring following acute pyelonephritis. J. Infect. Dis. 182:1738–1748.

47. Saurer, L., P. Reber, T. Schaffner, M. W. Buchler, C. Buri, A. Kappeler, A. Walz, H. Friess, and C. Mueller. 2000. Differential expression of chemokines in normal pancreas and in chronic pancreatitis. Gastroenterol. 118: 356–367.

48. Szekanecz, Z., R. M. Strieter, S. L. Kunkel, and A. E. Koch. 1998. Chemokines in rheumatoid arthritis. Springer Semin. Immunopathol. 20:115–132.

49. MacDermott, R. P. 1999. Chemokines in the inflammatory bowel diseases. J .Clin. Immunol. 19:266–272.

50. Damas, J. K., L. Gullestad, T. Ueland, N. O. Solum, S. Simonsen, S. S. Froland, and P. Aukrust. 2000. CXC-chemokines, a new group of cytokines in congestive heart failure—possible role of platelets and monocytes. Cardiovasc. Res. 45:428–436.

51. Morsey, M., Y. Popowych, J. Kowalski, G. Gerlach, D. Godson, M. Campos, and L. Babiuk. 1996. Molecular cloning and expression of bovine interleukin-8. Microbial Pathogen. 20:203–212.

52. Benson, M., I. L. Strannegard, G. Wennergren, and O. Strannegard. 1999. Interleukin-5 and interleukin-8 in relation to eosinophils and neutrophils in nasal fluids from school children with seasonal allergic rhinitis. Pediatr. Allergy Immunol. 10:178–185.

53. Hauser, U., M. Wagenmann, C. Rudack, and C. Bachert. 1997. Specific immunotherapy suppresses IL-8-levels in nasal secretions: A possible explanation for the inhibition of eosinophil migration. Allergol. 20:184–191.

54. Sehmi, R., O. Cromwell, A. J. Wardlaw, R. Moqbel, and A. B. Kay. 1993. Interleukin-8 is a chemoattractant for eosinophils purified from subjects with a blood eosinophilia but not from normal healthy subjects. Clin. Exp. Allergy 23:1027–1036.

55. Ulfinan, L. H., D. P. Joosten, J. A. van der Linden, J. W. Lammers, J. J. Zwaginga, and L. Koenderman. 2001. IL-8 induces a transient arrest of rolling eosinophils on human endothelial cells. J. Immunol. 166:588–595.

APPENDIX bovine CXCL8$_{(3-73)}$

ACA GAA CTT CGA TGC CAA TGC ATA AAA ACA CAT TCC ACA CCT TTC
CAC CCC AAA TTT ATC AAA GAA TTG AGA GTT ATT GAG AGT CCG CCA
CAC TGT GAA AAT TCA GAA ATC ATT GTT AAG CTT ACC AAT GGA AAC
GAG GTC TGC TTA AAC CCC AAG GAA AAG TGG GTG CAG AAG GTT GTG
CAG GTA TTT GTG AAG AGA GCT GAG AAG CAA GAT CCA bovine CXCL8$_{(3-73)}$K11R ACA GAA CTT CGA TGC CAG TGC ATA AGA ACA CAT TCC ACA CCT TTC
CAC CCC AAA TTT ATC AAA GAA TTG AGA GTT ATT GAG AGT GGG CCA
CAC TGT GAA AAT TCA GAA ATC ATT GTT AAG CTT ACC AAT GGA AAC
GAG GTC TGC TTA AAC CCC AAG GAA AAG TGG GTG CAG AAG GTT GTG
CAG GTA TTT GTG AAG AGA GCT GAG AAG CAA GAT CCA bovine CXCL8$_{(3-73)}$K11R/G31P ACA GAA CTT CGA TGC CAG TGC ATA AGA ACA CAT TCC ACA CCT TTC
CAC CCC AAA TTT ATC AAA GAA TTG AGA GTT ATT GAG AGT CCG CCA
CAC TGT GAA AAT TCA GAA ATC ATT GTT AAG CTT ACC AAT GGA AAC
GAG GTC TGC TTA AAC CCC AAG GAA AAG TGG GTG CAG AAG GTT GTG
CAG GTA TTT GTG AAG AGA GCT GAG AAG CAA GAT CCA bovine CXCL8$_{(3-73)}$K11R/G31P/P32G ACA GAA CTT CGA TGC CAG TGC ATA AGA ACA CAT TCC ACA CCT TTC
CAC CCC AAA TTT ATC AAA GAA TTG AGA GTT ATT GAG AGT CCG GGA
CAC TGT GAA AAT TCA GAA ATC ATT GTT AAG CTT ACC AAT GGA AAC
GAG GTC TGC TTA AAC CCC AAG GAA AAG TGG GTG CAG AAG GTT GTG
CAG GTA TTT GTG AAG AGA GCT GAG AAG CAA GAT CCA bovine CXCL8$_{(3-73)}$K11R/T12S/H13F/G31P ACA GAA CTT CGA TGC CAG TGC ATA AGA TCA TTT TCC ACA CCT TTC CAC CCC AAA TTT ATC AAA GAA TTG AGA GTT ATT GAG AGT GGA CCA CAC CGT GAA AAT TCA GAA ATC ATT GTT AAG CTT ACC AAT GGA AAC GAG GTC TGC TTA AAC CCC AAG GAA AAG TGG GTG CAG AAG GTT GTG CAG GTA TTT GTG AAG AGA GCT GAG AAG CAA GAT CCA 56. White JR, Lee JM, Dede K, Imburgia CS, Jurewicz AJ, Chan G, Fornwald JA, Dhanak D, Christmann LT, Darcy MG, Widdowson KL, Foley JJ, Schmidt DB, Sarau HM. 2000. Identification of potent, selective non-peptide CC chemokin receptor-3 antagonist that inhibits eotaxin-, eotaxin-2-, and monocyte chemotactic protein-4-induced eosinophil migration. J. Biol Chem. 275(47):36626-31.

57. Wells TN, Power CA, Lusti-Narasimhan M, Hoogewerf AJ, Cooke RM, Chung CW, Peitsch MC, Proudfoot AE. 1996. Selectivity and antagonism of chemokine receptors. J Leukoc Biol. 59(1):53-60.

What is claimed is:

1. An isolated ELR-CXC chemokine antagonist, consisting of the amino acid sequence set forth in SEQ ID NO:1.

2. An isolated ELR-CXC chemokine antagonist consisting of the amino acid sequence as set forth in SEQ ID No. 1 but wherein amino acid 30 of SEQ ID NO:1 is Gly instead of Pro and amino acid 29 of SEQ ID NO: 1 is glycine instead of proline.

3. An isolated ELR-CXC chemokine antagonist consisting of the amino acid sequence as set forth in SEQ ID No. 1 but wherein amino acid 10 of SEQ ID NO:1 is Ser instead of Thr and amino acid 11 of SEQ ID NO: 1 is Phe instead of His.

4. An isolated ELR-CXC chemokine antagonist consisting of the amino acid sequence as set forth in SEQ ID No. 1 but wherein amino acid 11 of SEQ ID NO:1 is Phe instead of His, amino acid 10 of SEQ ID NO:1 is Ser instead of Thr, amino acid 30 of SEQ ID NO:1 is Gly instead of Pro and amino acid 29 of SEQ ID NO:1 is glycine instead of proline.

5. A method for treating an ELR-CXC chemokine-mediated pathology, said pathology selected from the group consisting of acute respiratory distress syndrome, bacterial pneumonia and mastitis, in which an ELR-CXC chemokine binds to CXCR1 or CXCR2 receptors in a mammal, the method comprising administering to said mammal an effective amount of the ELR-CXC chemokine antagonist as recited in claim 1.

6. The method of claim 5, wherein the pathology is acute respiratory distress syndrome.

* * * * *

SEQUENCE LISTING

```
<160> NUMBER OF SEQ ID NOS: 8

<210> SEQ ID NO 1
<211> LENGTH: 72
<212> TYPE: PRT
<213> ORGANISM: Bos taurus

<400> SEQUENCE: 1

Thr Glu Leu Arg Cys Gln Cys Ile Arg Thr His Ser Thr Pro Phe His
1               5                   10                  15

Pro Lys Phe Ile Lys Glu Leu Arg Val Ile Glu Ser Pro Pro His Cys
            20                  25                  30

Glu Asn Ser Glu Ile Ile Val Lys Leu Thr Asn Gly Asn Glu Val Cys
        35                  40                  45

Leu Asn Pro Lys Glu Lys Trp Val Gln Lys Val Val Gln Val Phe Val
    50                  55                  60

Lys Arg Ala Glu Lys Gln Asp Pro
65                  70


<210> SEQ ID NO 2
<211> LENGTH: 74
<212> TYPE: PRT
<213> ORGANISM: Bos taurus

<400> SEQUENCE: 2

Met Ser Thr Glu Leu Arg Cys Gln Cys Ile Lys Thr His Ser Thr Pro
1               5                   10                  15

Phe His Pro Lys Phe Ile Lys Glu Leu Arg Val Ile Glu Ser Gly Pro
            20                  25                  30

His Cys Glu Asn Ser Glu Ile Ile Val Lys Leu Thr Asn Gly Asn Glu
        35                  40                  45

Val Cys Leu Asn Pro Lys Glu Lys Trp Val Gln Lys Val Val Gln Val
    50                  55                  60

Phe Val Lys Arg Ala Glu Lys Gln Asp Pro
65                  70


<210> SEQ ID NO 3
<211> LENGTH: 222
<212> TYPE: DNA
<213> ORGANISM: Bos taurus
<220> FEATURE:
<221> NAME/KEY: CDS
<222> LOCATION: (1)..(222)
<223> OTHER INFORMATION:

<400> SEQUENCE: 3

atg agt aca gaa ctt cga tgc caa tgc ata aaa aca cat tcc aca cct       48
Met Ser Thr Glu Leu Arg Cys Gln Cys Ile Lys Thr His Ser Thr Pro
1               5                   10                  15

ttc cac ccc aaa ttt atc aaa gaa ttg aga gtt att gag agt ggg cca       96
Phe His Pro Lys Phe Ile Lys Glu Leu Arg Val Ile Glu Ser Gly Pro
            20                  25                  30

cac tgt gaa aat tca gaa atc att gtt aag ctt acc aat gga aac gag      144
```

-continued

```
His Cys Glu Asn Ser Glu Ile Ile Val Lys Leu Thr Asn Gly Asn Glu
        35                  40                  45

gtc tgc tta aac ccc aag gaa aag tgg gtg cag aag gtt gtg cag gta      192
Val Cys Leu Asn Pro Lys Glu Lys Trp Val Gln Lys Val Val Gln Val
    50                  55                  60

ttt gtg aag aga gct gag aag caa gat cca                              222
Phe Val Lys Arg Ala Glu Lys Gln Asp Pro
65                  70


<210> SEQ ID NO 4
<211> LENGTH: 216
<212> TYPE: DNA
<213> ORGANISM: Bos taurus
<220> FEATURE:
<221> NAME/KEY: CDS
<222> LOCATION: (1)..(216)
<223> OTHER INFORMATION:

<400> SEQUENCE: 4

aca gaa ctt cga tgc caa tgc ata aga aca cat tcc aca cct ttc cac       48
Thr Glu Leu Arg Cys Gln Cys Ile Arg Thr His Ser Thr Pro Phe His
1               5                   10                  15

ccc aaa ttt atc aaa gaa ttg aga gtt att gag agt ccg cca cac tgt       96
Pro Lys Phe Ile Lys Glu Leu Arg Val Ile Glu Ser Pro Pro His Cys
            20                  25                  30

gaa aat tca gaa atc att gtt aag ctt acc aat gga aac gag gtc tgc      144
Glu Asn Ser Glu Ile Ile Val Lys Leu Thr Asn Gly Asn Glu Val Cys
        35                  40                  45

tta aac ccc aag gaa aag tgg gtg cag aag gtt gtg cag gta ttt gtg      192
Leu Asn Pro Lys Glu Lys Trp Val Gln Lys Val Val Gln Val Phe Val
    50                  55                  60

aag aga gct gag aag caa gat cca                                      216
Lys Arg Ala Glu Lys Gln Asp Pro
65                  70


<210> SEQ ID NO 5
<211> LENGTH: 45
<212> TYPE: DNA
<213> ORGANISM: Artificial Sequence
<220> FEATURE:
<223> OTHER INFORMATION: upstream primer

<400> SEQUENCE: 5

cagaacttcg atgccagtgc ataagatcat tttccacacc tttcc                      45


<210> SEQ ID NO 6
<211> LENGTH: 43
<212> TYPE: DNA
<213> ORGANISM: Artificial Sequence
<220> FEATURE:
<223> OTHER INFORMATION: upstream primer

<400> SEQUENCE: 6

gagagttatt gagagtccgc cacactgtga aaattcagaa atc                        43


<210> SEQ ID NO 7
<211> LENGTH: 43
<212> TYPE: DNA
<213> ORGANISM: Artificial Sequence
<220> FEATURE:
<223> OTHER INFORMATION: upstream primer

<400> SEQUENCE: 7

gagagttatt gagagtgggg gacactgtga aaattcagaa atc                        43
```

-continued

```
<210> SEQ ID NO 8
<211> LENGTH: 43
<212> TYPE: DNA
<213> ORGANISM: Artificial Sequence
<220> FEATURE:
<223> OTHER INFORMATION: upstream primer

<400> SEQUENCE: 8

gagagttatt gagagtccgg gacactgtga aaattcagaa atc                   43
```